United States Patent [19]

Robinson et al.

[11] 4,334,055

[45] Jun. 8, 1982

[54] RESIN DERIVED FROM ACENAPHTHENE, PROCESS FOR ITS PRODUCTION AND INTERMEDIATES IN ITS PRODUCTION

[75] Inventors: Joseph G. Robinson, Winchcombe; Sally A. Brain, Evesham, both of England

[73] Assignee: Coal Industry (Patents) Limited, London, England

[21] Appl. No.: 292,037

[22] Filed: Aug. 11, 1981

[30] Foreign Application Priority Data

Aug. 29, 1980 [GB] United Kingdom ................. 8027953

[51] Int. Cl.³ .............................................. C08G 12/00
[52] U.S. Cl. ................................... 528/229; 528/235; 528/247; 528/266
[58] Field of Search ................ 528/229, 235, 247, 266

[56] References Cited

U.S. PATENT DOCUMENTS

| | | | |
|---|---|---|---|
| 2,954,360 | 9/1960 | Krzikalla et al. | 528/247 X |
| 3,165,558 | 1/1965 | Imoto et al. | 528/247 X |
| 3,303,167 | 2/1967 | Kakiuchi et al. | 528/247 X |
| 3,513,221 | 5/1970 | Huang et al. | 528/247 X |
| 3,714,131 | 1/1973 | Hoback et al. | 528/229 X |
| 3,755,254 | 8/1973 | Zellner | 528/229 X |
| 3,767,616 | 10/1973 | Zellner | 528/229 X |

*Primary Examiner*—Lucille M. Phynes
*Attorney, Agent, or Firm*—Stevens, Davis, Miller & Mosher

[57] ABSTRACT

The invention relates to a novel resin derived from acenaphthene and to process for its production.

The resin comprises oligomers of naphthalic acid groups bridged by substantially only keto groups, the oligomers being joined together with a di- or tetra-functional primary aromatic amine and having been derived from a resin produced by acid-catalyzed condensation of acenaphthene and a formaldehyde donor.

It is envisaged that the resin will be of use in the preparation of drogue parachutes and in other circumstances where a thermally stable resin is required.

10 Claims, 1 Drawing Figure

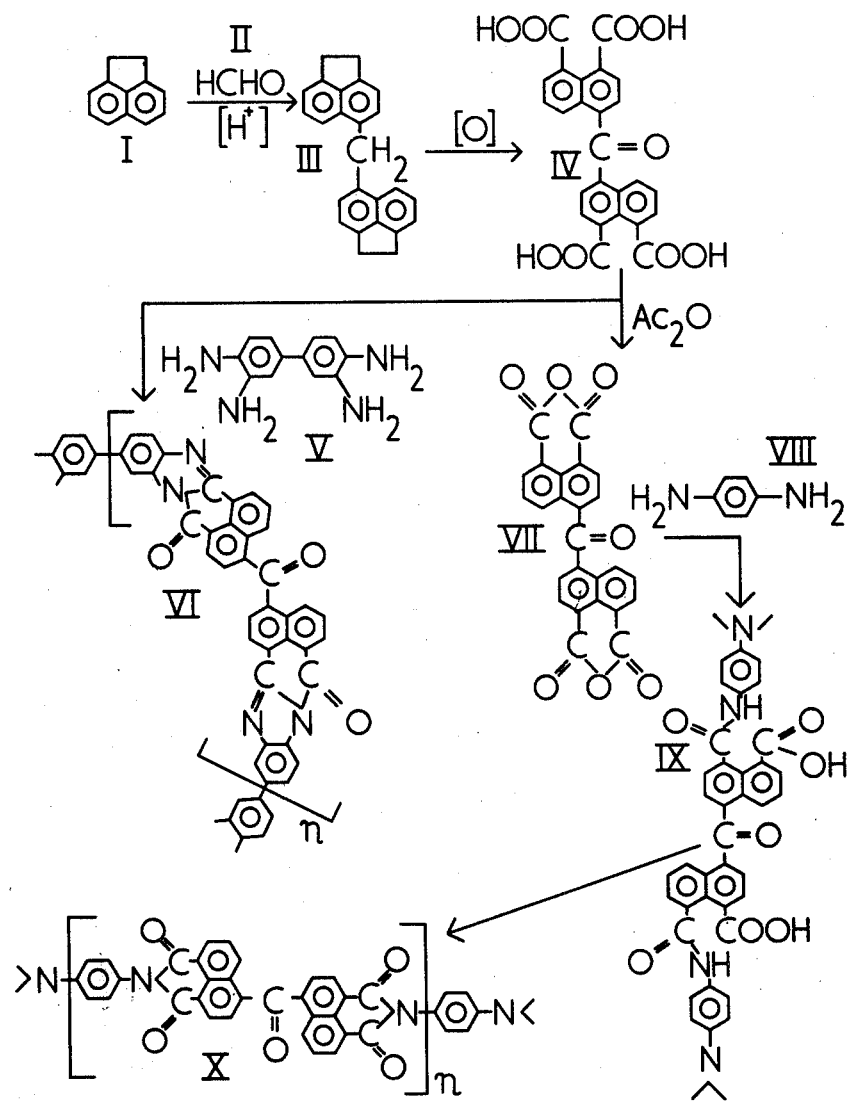

RESIN DERIVED FROM ACENAPHTHENE, PROCESS FOR ITS PRODUCTION AND INTERMEDIATES IN ITS PRODUCTION

This invention relates to a novel resin derived from acenaphthene and to a process for its production. The invention also includes intermediates for use in its production.

At present drogue parachutes for spacecraft are made using fibres of a pyrrone polymer known as Pyrrone BBB. This material is thought to be poly-(benzimidazobenzophenanthroline) dione, and retains some strength at temperatures up to 700°C. Pyrrone BBB is said to be produced from pyrene which is isolated from coal tar. Since the separation of pure pyrene from coal tar is difficult, the cost of Pyrrone BBB is very high. It is therefore desirable to be able to produce a product of similar thermal stability to Pyrrone BBB from a more readily available starting material.

It is therefore an object of the present invention to produce a resin which is at least thermally equivalent to Pyrrone BBB from more readily available source.

According to a first aspect of the present invention a process for the production of a novel thermally stable resin comprises the steps of:

(1) reacting acenaphthene with a formaldehyde donor in the presence of an acid catalyst to produce a low molecular weight resin comprising oligomers of acenaphthene moities joined by substantially only methylene bridges;

(2) oxidising the low molecular weight resin to form an intermediate resin comprising naphthalic acid units joined by keto bridges; and (3) reacting the intermediate resin with a di- or tetrafunctional primary aromatic amine to produce the thermally stable resin.

Preferably, where the intermediate resin is to be reacted with a difunctional amine, it is first dehydrated to produce its anhydride derivative.

The present invention also includes, in other aspects, the thermally stable resin produced by the process, the intermediate resin and its anhydride derivative.

The thermally stable resin produced by the process will be either a polymide, if made using a difunctional amine, or a benzimidazodione, if made using a tetrafunctional amine. The resin may be linear or cross-linked.

According to another aspect of the present invention there is provided a thermally stable resin comprising oligomers of naphthalic acid groups bridged by substantially only keto groups, the oligomers being joined together with a di- or tetra-functional primary aromatic amine wherein the oligomers are derived from a resin produced by the acid-catalysed condensation of acenaphthene and a formaldehyde donor.

In step (1) of the process described above, the molar ratio of formaldehyde to acenaphthene should be in the range 4:1 to 0.3:1 and is preferably about 0.5:1. The formaldehyde donor may be formaldehyde itself, paraformaldehyde or trioxane. The acid catalyst may be sulphuric acid or a Lewis acid such as aluminium chloride. Conveniently, the condensation reaction is carried out at a temperature from 30° to 95° C. for a time from 5 minutes to 8 hours. Preferably, the reaction is carried out in glacial acetic acid, since the condensation resin is insoluble in this medium and is therefore precipitated as it is formed.

The oxidation reaction of step (2) may be carried out using an organic peroxy acid such as peroxy acetic acid, but is preferably carried out using an inorganic oxidising agent, such as acid dichromate.

The intermediate resin may then be reacted directly with a tetrafunctional amine such as 3,4,3',4' tetraaminodiphenyl or 2,3,2',3' tetraaminodiphenylmethane.

The dehydration of the intermediate resin to produce an anhydride derivative for reaction with a difunctional amine is preferably carried out using an organic acid anhydride as the dehydrating agent. For instance, acetic anhydride is particularly suitable.

The difunctional amine for reaction with the anhydride derivative may be for instance 1,4 diaminobenzene or di-(4-aminophenyl) methane. Preferably the anhydride derivative is first treated with the diamine at a relatively low temperature, about 100° C., to form a polyamic acid. The polyamic acid is subsequently heated to about 300° C. whereupon cyclisation occurs, yielding a polyimide resin.

The thermally stable resin of the present invention, especially if formed using a tetrafunctional amine, is envisaged as being of particular, but not exclusive, use in the production of, for instance, drogue parachutes. However, it will also find use in applications demanding good thermal stability and retention of physical properties at temperatures up to 700° C.

If the resin is formed using a difunctional amine, it is likely to be less stable and may only be useful at temperatures up to about 500° C.

The invention will now be described by way of example only with reference to the accompanying drawing which shows a reaction scheme for the formation of a polyimide and a benzimidazodione resin.

Referring now to the drawing, there is shown a reaction scheme which the applicants believe illustrates the reactions involved in the process of the present invention. However, the applicants do not wish to be limited to this reaction mechanism, since the process may proceed by other routes.

Acenaphthene (I) and formaldehyde (II) react together in the presence of an acid catalyst to form a low molecularweight resin (III) comprising from two to about six acenaphthene units linked by methylene bridges. On oxidation the acenaphthene units are converted to naphthalic acid units and the methylene bridges are oxidised to carbonyl bridges, thus producing an intermediate resin (IV). The intermediate resin may then be reacted directly with a tetrafunctional primary aromatic amine (V) to yield a benzimidazodione resin (VI).

The intermediate resin may be dehydrated to produce its anhydride derivative (VII) which reacts with an aromatic primary diamine (VIII) to form first a polyamic acid (IX) and then a polyimide resin (X).

In practical terms, thermally stable resins are prepared as follows:

EXAMPLE 1

Acenaphthene (9.5 g) dissolved in glacial acetic acid (200 ml) was placed in a 500 ml flanged flask fitted with a stirrer and reflux condenser. To this was added a mixture containing paraformaldehyde (87% HCHO) (1.63 g) dissolved in sulphuric acid (98% w/w) (12.5 g) and distilled water (1.9 g). The flask was heated in an oil bath maintained at a temperature of either 40° or 60° C. The molar ratio of formaldehyde to acenaphthene was 0.74:1.

The reaction time was taken from the point of mixing the water/sulphuric acid/paraformaldehyde with the acenaphthene in acetic acid, to the removal of the flask from the oil bath. At the end of the reaction the contents of the flask were added to toluene (100 g) and, after stirring for 5 minutes, the mass was filtered to separate the soluble and insoluble fractions. The toluene solution was thereafter washed with water and dilute sodium carbonate solution until its pH reached about 8.0. Thereafter the toluene was removed by distillation, facilitated by passing nitrogen through the solution. The resin was then characterised and the data obtained are given in Table 1.

EXAMPLE 2

The procedure describe in Example 1 above, was repeated except that toluene was replaced by 1:2-dichloroethane. The solution obtained was washed, as previously, with water and then dilute sodium carbonate solution until the water decanted had a pH of about 8.0. The dichloroethane was then removed by distillation to yield resins whose properties are given in Table 2.

EXAMPLE 3

The procedure described in Example 2 above was repeated except that 98% sulphuric acid was used without the addition of 1.9 g distilled water. Also, lower reaction temperatures were employed. Apart from these modifications all other reaction conditions were maintained as previously. The experimental conditions and the properties of the resins obtained are shown in Table 3.

EXAMPLE 4

The procedure described in Example 3 was repeated except that the molar ratio of formaldehyde to acenaphthene was reduced from 0.76 to 0.5. Under these conditions the resins obtained had the properties given in Table 4.

RESIN PREPARATION

Selected resins from all of the methods were characterised by gel permeation chromatography which indicated that they comprised dimers, trimers, tetramers and higher oligomers of acenaphthene units joined by methylene bridges. The dimer was separated in each case and bulked together. This product was then converted to a polyimide, using the following procedure.

The dimer was oxidised with acid dichromate to give keto bridged di-naphthalic acid. This was then converted to the corresponding anhydride by reaction with acetic anhydride and then reacted with 1:4-diaminobenzene to yield the polyamic acid. On heating at 300° C. the polyamic acid was converted to a thermally stable linear polyimide.

The product was also converted into a benzimidazodione resin. The dimer was oxidised with acid dichromate to give keto bridged di-naphthalic acid, which was reacted at 100° with 3,4,3',4'. tetraaminodiphenyl. After reaction the material was heated to 300° C. to cause cyclisation, thus forming a benzimidazodione resin.

TABLE 1

| Temp (°C.) | Reaction Time (h) | Yield (%) | Molecular Weight (Average) | Free Acenaphthene (%) | Free Toluene (%) | Oxygen Content (%) |
| --- | --- | --- | --- | --- | --- | --- |
| 60 | 2 | 54 | 565 | 2.6 | 3.2 | 0.5 |
| 60 | 2 | 75 | 585 | 2.4 | 3.3 | 0.5 |
| 60 | 2 | 80 | 765 | 2.8 | 2.1 | 0.5 |
| 60 | 0.5 | 77 | 665 | 2.9 | 4.3 | 0.5 |
| 40 | 2 | — | 590 | 2.9 | 1.3 | 0.5 |
| 40 | 2 | 66 | 590 | 2.4 | 3.4 | 0.5 |

TABLE 2

| Mass Temp (°C.) | Reaction Time (h) | Yield (%)* | Molecular Weight (Average) | Oxygen content (%) | Free acenaphthene content (%) |
| --- | --- | --- | --- | --- | --- |
| 40 | 0.5 | 92 | 680 | 0.7 | 11.2 |
| 40 | 0.5 | 91 | 820 | 0.50 | 12.0 |
| 40 | 2 | 98 | 875 | 1.1 | 4.1 |
| 40 | 2 | 96 | 970 | 0.50 | 5.6 |
| 60 | 5 min | 90 | 1015 | 0.5 | 12.1 |
| 60 | 5 min | 87 | 865 | 0.9 | 11.7 |
| 60 | 0.5 | 93 | 600 | 0.50 | 4.3 |
| 60 | 0.5 | 91 | 1240 | 1.9 | 6.1 |
| 60 | 2 | 89 | 635 | 0.50 | 8.4 |
| 60 | 2 | 96 | 880 | 0.50 | 5.0 |
| 60 | 2 | 87 | 1390 | 0.8 | 6.1 |
| 95 | 0.5 | 95 | 3380 | 1.3 | 13.8 |
| 95 | 0.5 | 101 | 2450 | 0.6 | 6.2 |
| 95 | 2 | 103 | 5780 | 0.6 | 4.9 |
| 95 | 2 | 103 | — | 1.7 | 8.3 |

*Based on weight of acenaphthene.

TABLE 3

| Mass Temp (°C.) | Reaction Time (h) | Yield (%) | Molecular Weight (Average) | Oxygen content (%) | Free acenaphthene content (%) |
| --- | --- | --- | --- | --- | --- |
| 30 | 0.5 | 84 | 760 | 1.1 | 18.0 |
| 30 | 0.5 | 84 | 640 | 1.1 | 18.9 |
| 30 | 2 | 93 | 7920 | 0.6 | 11.8 |
| 30 | 2 | 91 | 1160 | 0.8 | 11.5 |
| 40 | 0.5 | 98 | 900 | 0.9 | 7.6 |
| 40 | 0.5 | 95 | 1705 | 0.5 | 8.2 |

TABLE 4

| Temp (°C.) | Reaction Time (h) | Yield (%) | Molecular Weight (Average) | Oxygen Content (%) | Free ace-content (%) |
| --- | --- | --- | --- | --- | --- |
| 40 | 0.5 | 71 | 875 | 0.5 | 30.7 |
| 40 | 0.5 | 67 | 790 | 1.1 | 34.6 |
| 40 | 2 | | | | |
| 40 | 2 | 78 | 1025 | 0.8 | 25.7 |

We claim:
1. A process for the production of a thermally stable resin comprising the steps of:
 (1) reacting acenaphthene with a formaldehyde donor in the presence of an acid catalyst to produce a low molecular weight resin comprising oligomers of acenaphthene moieties joined by substantially only methylene bridges;
 (2) oxidising the low molecular weight resin to form an intermediate resin comprising naphthalic acid units joined by keto bridges; and

(3) reacting the intermediate resin with a di- or tetra-functional primary aromatic amine to produce the thermally stable resin.

2. A process according to claim 1, and including the step of dehydrating the intermediate resin to its anhydride derivative prior to reacting it with a primary aromatic diamine.

3. A process according to claim 2, wherein the dehydration is carried out using an organic acid anhydride.

4. A process according to claim 1, wherein, in step (1), the molar ratio of formaldehyde to acenaphthene is in the range from 4:1 to 0.3:1.

5. A process according to claim 1, wherein step (1) is carried out in glacial acetic acid.

6. A process according to claim 1, wherein the oxidation in step (2) is carried out using acid dichromate.

7. A thermally stable resin made according to the process of claim 1.

8. A thermally stable resin comprising oligomers of naphthalic acid groups bridged by substantially only keto groups, the oligomers being joined together with a di- or tetra-functional primary aromatic amine and having been derived from a resin produced by acid-catalysed condensation of acenaphthene and a formaldehyde donor.

9. A thermally stable resin according to claim 8, wherein the oligomers are joined into linear polymers by the amine.

10. A thermally stable resin according to claim 8, wherein the oligomers are joined into cross-linked polymers by the amine.

* * * * *